(12) United States Patent
Nagy

(10) Patent No.: US 6,780,807 B2
(45) Date of Patent: Aug. 24, 2004

(54) ACYCLIC ANIONIC SIX-ELECTRON-DONOR ANCILLARY LIGANDS

(75) Inventor: Sandor M. Nagy, Naperville, IL (US)

(73) Assignee: Equistar Chemicals L.P., Houston, TX (US)

( * ) Notice: Subject to any disclaimer, the term of this patent is extended or adjusted under 35 U.S.C. 154(b) by 81 days.

(21) Appl. No.: 10/066,983

(22) Filed: Feb. 4, 2002

(65) Prior Publication Data

US 2003/0187160 A1 Oct. 2, 2003

(51) Int. Cl.$^7$ .............................. B01J 31/00; C07F 7/00; C08F 4/44
(52) U.S. Cl. ........................ 502/103; 502/117; 502/152; 502/153; 526/134; 526/160; 526/352; 526/943; 556/1; 556/7; 556/8; 556/19; 556/20; 556/27; 556/28; 556/176; 556/181
(58) Field of Search ........................... 556/7, 8, 19, 20, 556/27, 28, 1, 176, 181; 502/103, 117, 152, 153; 526/134, 160, 352, 943

(56) References Cited

U.S. PATENT DOCUMENTS

| | | | |
|---|---|---|---|
| 5,064,802 A | 11/1991 | Stevens et al. | 502/155 |
| 5,539,124 A | 7/1996 | Etherton et al. | 548/402 |
| 5,554,775 A | 9/1996 | Krishnamurti et al. | 556/7 |
| 5,599,761 A | 2/1997 | Turner | 502/152 |
| 5,637,659 A | 6/1997 | Krishnamurti et al. | 526/133 |
| 5,637,660 A | 6/1997 | Nagy et al. | 526/160 |
| 5,665,834 A * | 9/1997 | Srebnik et al. | 526/134 |
| 5,756,611 A | 5/1998 | Etherton et al. | 526/127 |
| 5,902,866 A | 5/1999 | Nagy et al. | 526/133 |

FOREIGN PATENT DOCUMENTS

DE          26 08 933          9/1977

OTHER PUBLICATIONS

D.S. Matteson and J.W. Wilson, *Organometallics* 1985, 4, 1690–1692, An αLithio Boronic Ester from an α–Trimethylstar Boronic Ester.

Carbanions from Deprotonation of α–(Phenylthio)alkaneboronic Esters, American Chemical Society, 1978, p. 1325.

D.S. Matteson and Karl H. Arne, Organometallics 1982, 1, 280–288, Carbanions from αPhenylthio Boronic Esters as Synthetic Intermediates, American Chemical Society.

D.S. Matteson and D. Majumdar, *Organometallics*, 1983, 2, 230–236, α–Trimethylsilyl Boronic Esters. Pinacol Lithio-(trimethylsilyl)methaneboronate, Homologation of Boronic Comparisons with Some Phosphorous and Sulfur Analogues.

G. Neumann and W.P. Neumann, Journal of Organometallic Chemistry, 1972, p. 293–306.

G. Zweifel and N.R. Pearson, *Thexylchloroborne. A Versatile Reagent for the Preparation of Mixed Thexyldiorganoboranes*, J. Am. Chem. Soc. 1980, 102, 5919–5920.

Sakai, Masaake et al; "Olefination and Hydroxymethylation of Aldehydes Using Knochel's (dialkoxyboryl)methylcopper reagents" Tetrahedron (1996), 52(3), 915–24, 1996, XP002233146, p. 919, compound 8.

Watanabe, Takeo et al., "Steroselective Synthesis of Allylic Boranates Via Palladium–Catalyzed Cross–Coupling Reaction of Knochel's (dialkoxyboryl)methylzinc Reagents Wtih 1–halo–1–alkenes", Journal of Organometallic Chemistry (1993), 444(1–2), C!–C3, 1993, XP002233147 compound 2.

Knochel, Paul, "A New Approach To Boron–Stabilized Organometallics", Journal of the American Chemical Society, (1990), 112(20), 7431–3, 1990, XP002233148.

Matteson, Donald S. et al., "Neighboring Boron In A Concerted Electrophilic Displacement", Journal of the American Chemical Society (1970), 92(6), 1801–3, 1970, xp002233149, Table 1.

Matteson, D.S. et al., "A New Synthesis Of An α–Haloakaneboronic Ester, 1–Bromo–1–Ethylenedioxyboryl–2–Phenylethane, and A Supervenient Synthesis of a 1,2–Diboronic Ester, 1,2–Bis(Ethylenedioxyboryl)–1–Phenylethane", Journal of Organometallic Chemistry, (1976), 114(1), 1–7, 1976, (XP002233150).

Pelter, Andrew et al., "Hindered Organoboron Groups In Organic Chemistry. 20. Alkylations and Acylations of Dimesitylboron Stabilized Carbanions", Tetrahedron (1993), 49(14), 2988–3006, 1993, XP002233151.

Garad, Manchak V. et al., "The Dimesitylboron Group In Organic Synthesis. 5. Heteroatom–Substituted Dimesitylborylmethanes", Tetrahedron Letters (1983), 24(6), 637–8 1983, XP000645485.

* cited by examiner

Primary Examiner—Porfirio Nazario-Gonzalez
(74) Attorney, Agent, or Firm—Brooks Kushman P.C.

(57) ABSTRACT

The present invention provides an improved acyclic anionic six-electron-donor ancillary ligand suitable for being bonded in a transition metal complex. The present invention also provides a transition metal complex that includes at least one acyclic anionic six-electron-donor ancillary ligand which is suitable for use as an olefin polymerization catalyst. The complex includes a Group 3 to 10 transition or lanthanide metal and one or more anionic or neutral ligands in an amount that satisfies the valency of the metal such that the complex has a net zero charge. The present invention also discloses a method for making transition metal complex and a method for using the complex for olefin polymerization.

23 Claims, No Drawings

ACYCLIC ANIONIC SIX-ELECTRON-DONOR ANCILLARY LIGANDS

BACKGROUND OF THE INVENTION

1. Field of the Invention

This invention relates to transition metal complexes with ancillary ligands, and in particular, to acyclic anionic six-electron donor ancillary ligands.

2. Background Art

The chemical industry uses a wide variety of transition metal complexes as catalysts for organic reactions. Olefin polymerization is an important example of such a reaction. While conventional Ziegler-Natta catalysts continue to dominate the industry, highly active metallocene or single-site catalysts which provide polymers with properties such as narrow molecular weight distributions, low densities, and good co-monomer incorporation, are emerging.

Transition metal complexes used to polymerize olefins are normally non-zero-valent metals (e.g., $Ti^{4+}$, $Zr^{4+}$, $Sc^{3+}$) surrounded by anionic ligands (e.g., chloride, alkyl, cyclopentadienyl) that satisfy the valency of the metal. The nature of the various anionic ligands can dramatically affect catalyst activity and polymer properties. Thus, by varying the choice of anionic ligand, a catalyst structure can be fine-tuned to produce polymers with desirable properties. Furthermore, the anionic ligand will affect the stability of the transition metal complexes.

Metallocene polymerization catalysts contain one or two cyclopentadienyl groups as anionic ligands. These serve to stabilize the active catalytic species, modulate the electronic and steric environment around the active metal center, and maintain the single-site nature of the catalyst. Polymers with narrow molecular weight and composition distributions may be produced using these metallocene catalysts. Such complexes frequently contain substituted cyclopentadienyl groups. By utilizing substituted cyclopentadienyl moieties, the geometry and electronic character of the active site may be altered, thus altering the activity and stability of the catalyst as well as the properties of the polyolefins produced therefrom.

Further anionic ligands are those which are heteroatomic ring ligands isolobal to the cyclopentadienyl ring; that is, the orbital interaction of the metal with the ligand is similar in both cases. Examples of such ligands are boraaryl (see, e.g., U.S. Pat. No. 5,554,775), pyrrolyl and indolyl anions (U.S. Pat. No. 5,539,124), azaborolinyl groups (U.S. Pat. No. 5,902,866), phospholyl anions, and tris(pyrazolyl)borate anions.

Transition metal complexes with highly delocalized cyclic anionic six-electron-donor ancillary ligands are important precursors for a variety of highly efficient catalysts. The performance and cost of these catalysts are strongly dependent on the structure of the ligands. It would be desirable to provide transition metal complex catalysts in addition to those presently available in order to provide further options with regard to catalytic activity and stability and polyolefin product properties.

SUMMARY OF THE INVENTION

In one embodiment of the present invention, a delocalized anionic acyclic ligand capable of providing six electrons when coordinated to a transition metal is provided. The structure of the ligand of the present invention is given by:

I where A is $CH_2$, $CHR^3$, $CR^3R^4$, $NR^3$, O, S, or $PR^3$; $R^1$ and $R^2$ are each independently hydrogen, an aryl group, preferably a $C_{6-15}$ aryl group, a $C_{6-15}$ arylphospho group (each aryl is $C_{6-5}$), a $C_{6-15}$ arylthio group, $C_{7-15}$ aralkyl group, $C_{1-10}$ alkoxy group, $C_{6-14}$ aryloxy group, a $C_{1-10}$ dialkylamino group (each alkyl is $C_{1-10}$), or a $C_{6-15}$ diarylamino group (each aryl is $C_{6-15}$); $R^3$ and $R^4$ are each independently hydrogen, a $C_{1-8}$ alkyl group, $C_{6-10}$ aryl group, or $C_{7-15}$ aralkyl group; and Y is B, Al, or Ga. It should be noted that in compounds containing "$C_{6-15}$ diaryl" groups and similar designations, the $C_{6-15}$ refers to each aryl group rather than the total carbon content of the ligand.

In another embodiment of the present invention, a transition metal complex incorporating the ligand of structure I is provided. The structure of the complex of the present invention is:

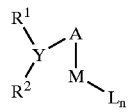

II where M is a transition metal; L is a sigma bonded or pi bonded ligand; n is an integer such that the valency of M is satisfied; A is $CH_2$, $CHR^3$, $CR^3R^4$, $NR^3$, O, S, and $PR^3$; $R^1$ and $R^2$ are each independently hydrogen, $C_{6-10}$ aryl, diarylphospho, $C_{1-8}$ alkylthio, $C_{6-15}$ arylthio, $C_{7-15}$ aralkyl, $C_{1-10}$ alkoxy group, $C_{6-14}$ aryloxy group, $C_{1-10}$ dialkylamino group, or $C_{6-15}$ diarylamino group; $R^3$ and $R^4$ are each independently hydrogen, $C_{1-8}$ alkyl, $C_{6-10}$ aryl, $C_{7-15}$ aralkyl, $C_{1-10}$ alkoxy, $C_{6-14}$ aryloxy, $C_{1-10}$ dialkylamino, or $C_{6-15}$ diarylamino, and Y is B, Al, or Ga.

In still another embodiment of the present invention, a method for forming the metal complex having the ligand of the present invention is provided. The method comprises reacting a ligand precursor having the following structure:

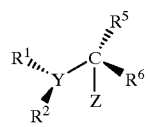

III where Z is a leaving group, with a metal compound with the structure:

IV where X is a halogen, to form metal complex II. L and n are as defined above.

DETAILED DESCRIPTION OF THE PREFERRED EMBODIMENTS

Reference will now be made in detail to presently preferred compositions or embodiments and methods of the invention, which constitute the best modes of practicing the invention presently known to the inventor. It should be noted that the term "six-electron-donor ancillary ligands" refers to ligands capable of bonding to a metal atom through six electrons.

In one embodiment of the present invention, a delocalized anionic acyclic ligand capable of providing six electrons while coordinated to a transition metal is provided. The structure of the ligand of the present invention is given by:

I where A is $CH_2$, $CHR^3$, $CR^3R^4$, $NR^3$, O, S, or $PR^3$; $R^1$ and $R^2$ are each independently hydrogen, $C_{6-10}$ aryl, a $C_{6-15}$ diarylphospho group (each aryl is $C_{6-15}$), a $C_{1-18}$ alkylthio group, a $C_{6-15}$ arylthio group, $C_{7-15}$ aralkyl group, $C_{1-10}$ alkoxy group, $C_{6-14}$ aryloxy group, a $C_{1-10}$ dialkylamino group (each alkyl is $C_{1-10}$), or $C_{6-15}$ diarylamino group (each aryl is $C_{6-15}$); $R^3$ and $R^4$ are each independently hydrogen, a $C_{1-8}$ alkyl group, $C_{6-10}$ aryl group, or $C_{7-15}$ aralkyl group; and Y is B, Al, or Ga. Furthermore, $R^1$ and $R^2$ may optionally be bonded to form a cyclic structure.

In a preferred embodiment of the present invention, the anionic ligand is given by the formula V:

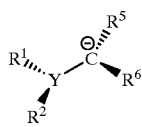

V where $R^1$ and $R^2$ are the same as above; $R^5$ and $R^6$ are independently hydrogen, a $C_{1-8}$ alkyl group, $C_{6-10}$ aryl group, $C_{7-15}$ aralkyl group, $C_{1-10}$ alkoxy group, $C_{6-14}$ aryloxy group, $C_{1-10}$ dialkylamino group, or $C_{6-15}$ diarylamino group. In a refinement of this embodiment a preferred ligand is given by formula VI:

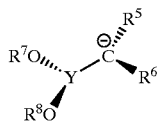

VI where $R^5$ and $R^6$ are the same as above; $R^7$ and $R^8$ are independently a $C_{1-18}$ alkyl group, $C_{6-10}$ aryl group, or $C_{7-15}$ aralkyl group. Examples of this refinement include but are not limited to compounds given by structures VII and VIII:

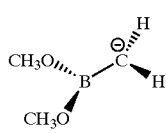

VII

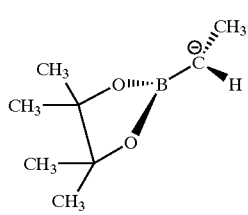

VIII

In another refinement of the ligand of structure V, a preferred ligand is given by structure IX:

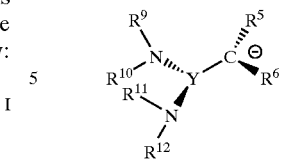

IX where $R^5$ and $R^6$ are the same as above and $R^9$, $R^{10}$, $R^{11}$, and $R^{12}$ are independently a $C_{1-8}$ alkyl group, $C_{6-10}$ aryl group, or $C_{7-15}$ aralkyl group.

Another preferred ligand is provided by the group illustrated by structure X:

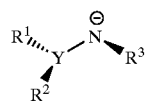

X where Y, $R^1$, $R^2$, and $R^3$ are as provided above. In a variation of this preferred embodiment, the anionic ligand is described by structure XI:

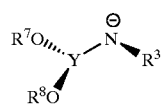

XI where Y, $R^3$, $R^7$, and $R^8$ are as provided above.

Another preferred ligand is provided by the group illustrated by structure XII:

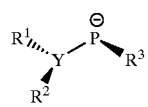

XII where Y, $R^1$, $R^2$, and $R^3$ are as provided above.

Another preferred ligand is provided by the group illustrated by structure XIII:

XIII where Y, $R^1$, and $R^2$ are as provided above.

Another preferred ligand is provided by the group illustrated by structure XIV:

XIV where Y, $R^1$, and $R^2$ are as provided above.

In another embodiment of the present invention, a transition metal complex incorporating the ligand of structure I is provided. The structure of the complex of the present invention is:

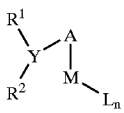

II where M is a transition metal; L is a sigma bonded or pi bonded ligand; n is an integer such that the valency of M is satisfied; A is $CH_2$, $CHR^3$, $CR^3R^4$, $NR^3$, O, S, and $PR^3$; $R^1$ and $R^2$ are each independently hydrogen, a $C_{6-15}$ diarylphospho group, a $C_{1-18}$ alkylthio group, a $C_{6-15}$ arylthio group, $C_{7-15}$ aralkyl group, $C_{1-10}$ alkoxy group, $C_{6-14}$ aryloxy group, $C_{1-10}$ dialkylamino group, or $C_{6-15}$ diarylamino group; and Y is B, Al, or Ga. The transition metal M is preferably a Group 3 to 10 transition or lanthanide metal. Preferred Group 3 to 10 metals comprise Sc, Ti, Cr, Mn, Fe, Co, Ni, and elements directly below these in the Periodic Table. Preferred lanthanide metals include La, Ce, Pr, Eu, Yb, and the like. More preferably, the transition metal complex comprises a Group 3 to 6 transition or lanthanide metal, and most preferably, a Group 4 transition metal. The sigma bonded or pi bonded ligands, L, are preferably one or more anionic or neutral ligands. The one or more anionic or neutral ligands are present in an amount determined by n such that the valency of M is satisfied. Examples include unsubstituted and substituted cyclopentadienyl, indenyl, fluorenyl, hydride, halide, alkyl, aryl, aralkyl, dialkylamino, siloxy, alkoxy, pyrrolyl, indolyl, carbazoyl, quinolinyl, pyridinyl, azaborolinyl, boraaryl groups, or the like, and combinations of these. Examples of neutral ligands are carbonyl, $\eta^6$-aryl, $\eta^4$-butadiene, $\eta^4$-cyclobutadiene, $\eta^4$-cyclooctatetraene, tertiary phosphine, and the like. Other examples of suitable anionic or neutral ligands appear in U.S. Pat. Nos. 5,756,611, 5,637,659, 5,637,660, 5,554,775, and 5,539,124, the teachings of which are incorporated herein by reference.

In a particularly preferred embodiment of the present invention, a transition metal complex having the anionic ligand of the present invention is provided by structure XV:

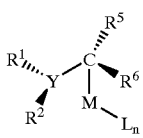

XV where $R^1$ and $R^2$ are as provided above; $R^5$ and $R^6$ are independently hydrogen, a $C_{1-18}$ alkyl group, $C_{6-10}$ aryl group, $C_{7-15}$ aralkyl group, $C_{1-10}$ alkoxy group, $C_{6-14}$ aryloxy group, $C_{1-10}$ dialkylamino group, or $C_{6-15}$ diarylamino group. In a refinement of this embodiment a preferred ligand is given by formula XVI:

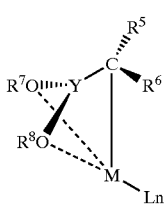

XVI where $R^5$ and $R^6$ are as provided above; $R^7$ and $R^8$ are independently a $C_{1-8}$ alkyl group, $C_{6-10}$ aryl group, or $C_{7-15}$ aralkyl group. Examples of this refinement include but are not limited to compounds given by structures XVII and XVIII:

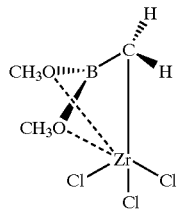

XVII

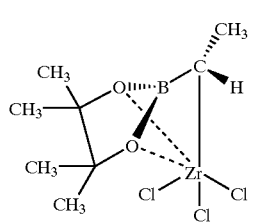

XVIII

Another particularly preferred complex is provided in structure XIX:

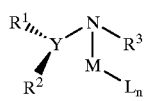

XIX where Y, $R^1$, $R^2$, and $R^3$ are as provided above. In a variation of this preferred embodiment, the anionic ligand is described by structure XX:

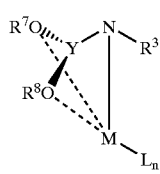

XX

Still another preferred metal complex is provided by structure XXI:

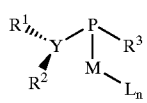

XXI where Y, M, n, $R^1$, $R^2$, and $R^3$ are as provided above.

Still another preferred embodiment of the present invention, is provided by the complex provided in structure XXII:

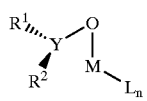

XXII where Y, M, n, $R^1$, and $R^2$ are as provided above.

Still another preferred embodiment of the present invention, is provided by the complex provided in structure XXIII:

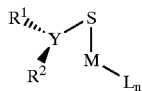

XXIII where Y, M, n, $R^1$, and $R^2$ are as provided above.

In another embodiment of the invention, the transition metal complex further comprises an activator. Generally, the activator converts the complex to a cationically active species. The catalysts are especially valuable for polymerizing olefins, such as ethylene, propylene, and/or other α-olefins such as 1-butene or 1-hexene. Suitable activators are well known in the art. Preferred activators include alumoxanes (e.g., methyl alumoxane (MAO), PMAO, ethyl alumoxane, diisobutyl alumoxane), alkylaluminum compounds (triethylaluminum, diethylaluminum chloride, trimethylaluminum), and the like. Such activators are generally used in an amount within the range of about 0.01 to about 100,000, preferably from about 1 to about 10,000, moles per mole of transition metal complex. Preferred activators also include acid salts that contain non-nucleophilic anions. These compounds generally consist of bulky ligands attached to boron or aluminum. Examples include lithium tetrakis(pentafluorophenyl) borate, lithium tetrakis(pentafluorophenyl) aluminate, anilinium tetrakis (pentafluorophenyl) borate, and the like. These activators are generally used in an amount within the range of about 0.01 to about 1000, preferably from about 1 to about 10, moles per mole of transition metal complex. Suitable activators also include trialkyl or triarylboron compounds such as tris(pentafluorophenyl)boron, tris(pentabromophenyl) boron, and the like. Other suitable activators are described, for example, in U.S. Pat. Nos. 5,756,611, 5,064,802, and 5,599,761, the teachings of which are incorporated herein by reference.

The catalysts are optionally used with an inorganic solid or organic polymer support. Suitable supports include silica, alumina, silica-aluminas, magnesia, titania, clays, zeolites, or the like. The supports can be pretreated thermally or chemically to improve catalyst productivity or product properties. The catalysts can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst. The ligand can also be chemically tethered to the support through a suitable linking group.

In yet another embodiment of the present invention, a method for forming the metal complex having the ligand of the present invention is provided. The method comprises reacting a ligand precursor having the following structure:

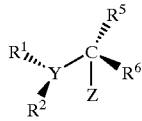

III with a metal compound with the structure:

X—M—Ln

IV where X is a halogen, to form metal complex II.

In another embodiment of the invention, an olefin polymerization process is provided. The process comprises polymerizing an olefin in the presence of a catalyst of the invention according to methods that are well known in the art. Suitable techniques include gas, high-pressure liquid, slurry, solution, or suspension-phase processes and combinations of these. Suitable olefins include ethylene, propylene, butenes, pentenes, hexenes, octenes, styrenes, 1,3-butadiene, norbornene, and the like. Preferred olefins are ethylene, propylene, and α-olefins such as 1-butene, 1-hexene, and 1-octene.

The following examples illustrate the various embodiments of the present invention. All reactions are carried out in an inert, air-free atmosphere using vacuum line or dry box. All solvents are dry and deoxygenated. Those skilled in the art will recognize many variations that are within the spirit of the present invention and scope of the claims.

EXAMPLE 1

Complex Formed by Reaction of Pinacol [1-(Trimethylstannyl)ethyl] Boronate With Cyclopentadienyl Zirconium Trichoride A slurry of 2.63 (0.01 moles) of cyclopentadienyl zirconium trichloride in 100 ml of toluene at dry ice temperature is combined with 3.25 g (0.01 moles) of pinacol [1-(trimethylstannyl)ethyl]boronate, prepared according to D. J. Matteson et al, *Organometallics*, v.4, p. 1690 (1985). The mixture is gradually warmed up to room temperature and refluxed for 24 hours. The residue after evaporation of toluene is washed with cold hexane and used in polymerization experiments without further purification.

EXAMPLE 2

Complex Formed by Reaction of Pinacol (1-lithioethyl) Borate With Cyclopentadienvl Zirconium To a cold (−100° C.) solution of pinacol (1-lithioethyl) borate in 100 ml of THF prepared according to reference 4 from 3.25 g (0.01 moles) of pinacol [1-(trimethylstannyl) ethyl]boronate 0.01 moles of THF complex of cyclopentadienyl zirconium trichloride is slowly added. The mixture is gradually warmed up at room temperature and stirred for 24 hours. The residue after evaporation of THF is used for polymerization without further purification.

EXAMPLE 3

Preparation of a Supported Catalyst

To 2 ml of 4.1 M solution of polymethylalumoxane in toluene 0.005 g of the complex formed in Example 1 is added and stirred for 1 hr at ambient temperature. The resulting solution is added slowly to stirred bed of dehydrated silica support to result in a free-flowing catalyst powder.

EXAMPLE 4

Polymerization of Ethylene

About 0.25 g of the supported catalyst formed in Example 3 is added to a 1000 ml reactor charged with 500 ml of isobutane and 1 ml of 2M solution of triisobutylaluminum in heptane and ethylene is polymerized at 350 psi ethylene pressure at 70° C. to produce high molecular weight polyethylene.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A composition of matter comprising a ligand having the formula:

where

A is $NR^3$, O, S, or $PR^3$; $R^1$ and $R^2$ are independently $C_{6-15}$ diaryiphospho, $C_{1-18}$ alkylthio, $C_{6-15}$ arylthio, $C_{1-10}$ alkoxy, $C_{6-14}$ aryloxy, $C_{1-10}$ dialkylamino, or $C_{6-15}$ diarylamino; $R^3$ and $R^4$ are independently hydrogen, $C_{1-8}$ alkyl, $C_{6-10}$ aryl; and Y is B, Al, or Ga.

2. The composition of claim 1 wherein said ligand has the formula:

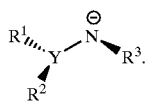

3. The composition of claim 2 wherein said ligand has the formula:

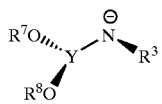

where $R^7$ and $R^8$ are independently $C_{1-8}$ alkyl, $C_{6-10}$ aryl, or $C_{7-15}$ aralkyl.

4. The composition of claim 1 wherein said ligand has the formula:

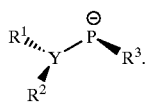

5. The composition of claim 1 wherein said ligand has the formula:

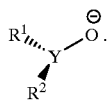

6. The composition of claim 1 wherein said ligand has the formula:

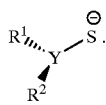

7. A polymerization catalyst comprising an activator and a complex having the formula:

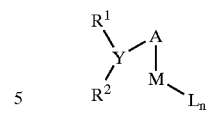

where

M is a Group 3 to 10 transition metal;

L is a sigma bonded or pi bonded ligand;

n is an integer such that the valency of M is satisfied;

A is $CH_2$, $CHR^3$, $CR^3R^4$, $NR^3$, O, S, and $PR^3$;

$R^1$ and $R^2$ are independently $C_{6-14}$ diarylphospho, $C_{1-18}$ alkylthio, $C_{6-15}$ arylthio, $C_{1-10}$ alkoxy, $C_{6-14}$ aryloxy, $C_{1-10}$ dialkylamino, or $C_{6-15}$ diarylamino;

$R^3$ and $R^4$ are independently hydrogen, $C_{1-8}$ alkyl, $C_{6-10}$ aryl, $C_{7-15}$ aralkyl, $C_{1-10}$ alkoxy, $C_{6-14}$ aryloxy, $C_{1-10}$ dialkylamino, or $C_{6-15}$ diarylamino; and Y is B, Al, or Ga.

8. The polymerization catalyst of claim 7 wherein said complex has the formula:

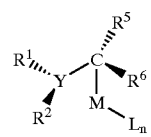

where:

$R^5$ and $R^6$ are independently hydrogen, a $C_{1-8}$ alkyl group, $C_{6-10}$ aryl group, $C_{7-15}$ aralkyl group, $C_{1-10}$ alkoxy group, $C_{6-14}$ aryloxy group, $C_{1-10}$ dialkylamino group, or $C_{6-15}$ diarylamino group.

9. The polymerization catalyst of claim 7 wherein said complex has the formula:

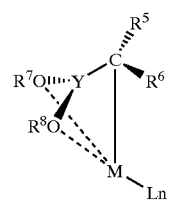

where $R^7$ and $R^8$ is hydrogen, a $C_{1-8}$ alkyl group, $C_{1-10}$ aryl group, or $C_{7-15}$ aralkyl group.

10. The catalyst of claim 7 wherein said complex has the formula:

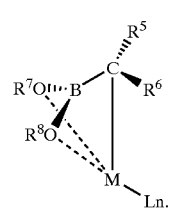

11. The catalyst of claim 7 wherein said complex has the formula:

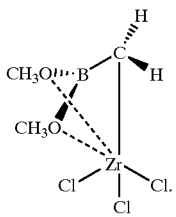

12. A catalyst comprising a complex having the structure:

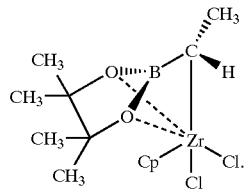

13. The catalyst of claim 7 wherein said complex has the formula:

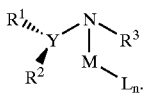

14. The catalyst of claim 7 wherein said complex has the formula:

where
R$^7$ and R$^8$ are independently a C$_{1-8}$ alkyl group, C$_{6-10}$ aryl group, or C$_{7-15}$ aralkyl group.

15. The catalyst of claim 7 wherein said complex has the formula:

16. The catalyst of claim 7 wherein said complex has the formula:

17. The catalyst of claim 7 wherein said complex has the formula:

18. A process for the oligomerization or polymerization of at least one α-olefin, said process comprising polymerizing said at least one α-olefin in the presence of a polymerization catalyst component comprising the polymerization catalyst of claim 7.

19. A polyolefin or oligoolefin prepared by the process of claim 18.

20. A composition of matter comprising a ligand having the formula:

where

R$^5$ and R$^6$ are independently hydrogen, a C$_{18}$ alkyl group, C$_{6-10}$ aryl group, C$_{7-15}$ aralkyl group, C$_{1-10}$ alkoxy group, C$_{6-14}$ aryloxy group, C$_{1-10}$ dialkylamino group, or C$_{6-15}$ diarylamino group R$^9$, R$^{10}$, R$^{11}$, and R$^{12}$ are independently C$_{1-8}$ alkyl, C$_{6-10}$ aryl, or C$_{7-15}$ aralkyl;

Y is B, Al, or Ga.

21. The catalyst of claim 7 wherein the transition metal is a Group 3 to Group 6 transition or lanthanide metal.

22. The catalyst of claim 7 wherein the transition metal is a Group 4 transition metal.

23. The catalyst of claim 7 wherein the activator is an alumoxane, and alkylaluminum compound, a trialkyl- or triaylboron compound, or an ionic borate or aluminate compound.

* * * * *

UNITED STATES PATENT AND TRADEMARK OFFICE
CERTIFICATE OF CORRECTION

PATENT NO.    : 6,780,807 B2
DATED         : August 24, 2004
INVENTOR(S)   : Sandor M. Nagy It is certified that error appears in the above-identified patent and that said Letters Patent is hereby corrected as shown below:

Column 10,
Line 15, delete "$C_{6-14}$ diarylphospho" and insert -- $C_{6-15}$ diarylphospho --.
Line 51, delete "$C_{1-10}$ aryl" and insert -- $C_{6-10}$ aryl --.

Column 11,
Line 1, insert

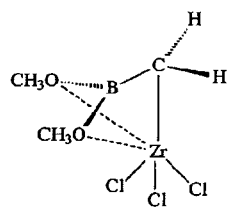

Column 12,
Line 35, delete "$C_{18}$ alkyl" and insert -- $C_{1-8}$ alkyl --.

Signed and Sealed this

Twenty-eighth Day of December, 2004

JON W. DUDAS
*Director of the United States Patent and Trademark Office*